(12) United States Patent
Lima (10) Patent No.: US 7,698,090 B2
(45) Date of Patent: Apr. 13, 2010

(54) SYSTEM FOR THE MEASURE OF THERMAL PROPERTIES OF FLUIDS

(76) Inventor: José Augusto Pedro Lima, c/o Banner & Witcoff, 10 S. Eacker Dr., Chicago, IL (US) 60606

(*) Notice: Subject to any disclaimer, the term of this patent is extended or adjusted under 35 U.S.C. 154(b) by 177 days.

(21) Appl. No.: 11/597,540

(22) PCT Filed: May 25, 2005

(86) PCT No.: PCT/BR2005/000093

§ 371 (c)(1),
(2), (4) Date: Jun. 12, 2007

(87) PCT Pub. No.: WO2005/116619

PCT Pub. Date: Dec. 8, 2005

(65) Prior Publication Data

US 2007/0288193 A1   Dec. 13, 2007

(30) Foreign Application Priority Data

May 25, 2004  (BR)  .................................... 0402805

(51) Int. Cl.
*G01K 17/00*  (2006.01)
(52) U.S. Cl. ..................................................... 702/136
(58) Field of Classification Search ................. 702/130, 702/136; 374/10, 11, 54, 57; 123/563; 600/316
See application file for complete search history.

(56) References Cited

U.S. PATENT DOCUMENTS 4,579,463 A    4/1986  Rosencwaig et al.
4,690,569 A    9/1987  Veitch
5,657,754 A    8/1997  Rosencwaig
5,940,784 A    8/1999  El-Husayni
5,988,875 A *  11/1999 Gershfeld et al. ............. 374/10
7,171,955 B2 * 2/2007  Perkins ........................ 123/563

FOREIGN PATENT DOCUMENTS

JP            1016953 A      1/1989

* cited by examiner

*Primary Examiner*—Tung S Lau
*Assistant Examiner*—Xiuquin Sun
(74) *Attorney, Agent, or Firm*—Fitch, Even, Tabin & Flannery (57) ABSTRACT

The present invention refers to a system, composed by mechanical and electronic components and by a resident software inherent to the system. The system for the mean of thermal properties of fluids is destinated to the measure of thermal properties such as diffusivity and effusivity, and from those values, to obtain the conductivity and the volume thermal capacity of flowing media. Besides the use for the direct measure of thermal properties, the referred system has application in the verification of the quality or of adulterations in fuels (octane and no conformity), fuel oils and lubricants, perfumes, foods, drunk, and working as humidity met gases. In these cases the essential feature is the correlation of the measure of thermal property and the quality parameter of the substance analyzed. The present invention can used in industries and laboratories.

23 Claims, 11 Drawing Sheets

SYSTEM FOR THE MEASURE OF THERMAL PROPERTIES OF FLUIDS

The present invention refers to a system that uses photothermal techniques to measure thermal properties of fluids by means of the propagation and interference of thermal waves. An application of this invention is directly related to the fluids analysis. Not only this application area, it is possible, by means of the measure of the thermal diffusivity and/or thermal effusivity, for example, to use the referred system for the verification of the quality (octane) or adulteration in fuels, perfumes, foods, not only working as a humidity and gases meter.

In a general way, photothermal phenomena are associated to 4 thermal properties and an optic one, in other words, the thermal conductivity ($\kappa$), thermal diffusivity ($\alpha$), thermal effusivity ($\epsilon$), volumetric thermal capacity ($\rho c$) and the optical absorption coefficient ($\beta$). The thermal and optical characterization of a sample (solid, liquid or gaseous), consists directly or indirectly on a tool to interpretation or correlation to other phenomena or physical properties of interest.

The working principle of the present invention is based on the propagation of thermal waves in a medium. The thermal waves concept, as well as its application, are already consolidated and used. They can be mentioned as example the methods and apparatuses used for the characterization of solid materials according to the references of EP 0163466A2, EP 0162681A2, EP 0102730A2, U.S. Pat. Nos. 4,690,569, 4,484,820, EP 0165711A2 and U.S. Pat. No. 4,513,384.

According to the invention, the basic working principle of the system for thermal properties measurement of fluids consists in generating, by means of a of "thermal waves generator", thermal waves front of impulse, step or periodic shape with frequencies can be set from 0.1 to 1000 Hz, that is generates from a surface, which may be preferably a thin metallic disk. In order to a thermal waves front can be produced, it is necessary that the disk receives a thin layer of a highly absorbent light coating just as it is "black of the soot". Not only this, to generating the thermal waves is necessary that the modulated radiation impinges on the blackened face.

Parallel located at the distance (L) in front of the surface of the thermal waves generator disk which is without covering, exists another surface, a disk, preferable made of $\beta$-polyvinyldielene fluoride (PVDF) metallic film. This pyroeletric film can detect temperature ripples of $10^{-6}K$ by the measuring of the alternated potential difference that appears between the metallic faces, and whose amplitude is function of geometric and electric parameters of the film and of the spatial average distribution of the temperature on it surface. According to the invention, the pyroeletric disk film not only working as a sensor, but it works also as a wall that partially promotes the thermal waves reflection turning back to the disk that generated them. For example, for a given frequency (f), and for a certain distance (L) located in the range from 0 to 5 mm, it can happen overlap of the thermal waves generated with the reflected thermal waves.

The theoretical expression of the signal generated on the sensor is $$S(K, \Gamma, L, \alpha, f) = K \frac{e^{-\sigma L}}{1 - \Gamma e^{-2\sigma L}}, \quad [1]$$

where K is a complex constant that depends on electric parameters of the pyroeletric film and of the measure circuit parameters; L is the distance between the pyroeletric sensor and the thermal waves generator; $\sigma = (1+i)\sqrt{\pi f/\alpha}$, f is the frequency of the thermal waves generator and $\alpha$ is thermal diffusivity of the medium.

The parameter $\sqrt{\pi f/\alpha}$ is denominated thermal diffusion length ($\mu$) and physically it represents the effective depth penetration of a thermal wave in a material or medium. The factor $\Gamma$, in the expression [1], is the normal incidence reflection coefficient of thermal waves that includes relationships among the thermal effusivity of the flowing medium, of the sensor pyroeletric and of the disk material. Therefore, by means of the variation of the distance L and a fixed thermal wave frequency f, t is possible to acquire experimental values from the signal of the sensor. By means of the statistical computational fit of the theoretical expression [1] to the measured points, it is obtained the value of the diffusivity ($\alpha$) and of the effusivity ($\epsilon$) and consequently the one of the thermal conductivity ($\kappa$) and the volumetric thermal capacity ($\rho c$) of the flowing medium.

In general, the signal levels involved in the measuring of these properties are very low intensity and they need an especial kind of processing.

In the practice, the circuit, instrument or software that performs this function is called synchronized amplifier (lock-in amplifier). Current or voltage signal measured by means to this technique, can be characterized by they values in phase and in quadrature (real and imaginary parts) or in amplitude (module) and phase. Both ways can be used to exhibit the signal graphics. More details can be seen in the works: On The Uses Of The Thermal Wave Resonator Cavity Sensor For Monitoring Hydrocarbon Vapors J. A. P. Lima, E. Marin, M. G. da Silva, M. S. Sthel, S. L. Cardoso, H. Vargas and L. C. M. Miranda *Rev. Sci. Inst,* 71, 7 (2000)., Characterization Of The Thermal Properties Of Gases Using Thermal Wave Interferometer J. A. P. Lima, E. Marin, M. G. Da Silva, M. S Sthel, D. U Schramm, S. L Cardoso, H. Vargas And L. C. M. Miranda *Meas. Sci. Technol,* 12, 1949-1955 (2000), Measurement Of Thermal Properties Of Liquids Using Thermal Wave Interferometer J. A. P. Lima, E. Marin, O. Correa, M. G. da Silva, S. L. Cardoso, C. Gatts, C. E. Rezende, H. Vargas and L. C. M. Miranda *Meas. Sci. Technol.* 11 1522-1526 (2000).

The present invention, uses preferentially the method called "made easy" for measuring thermal diffusivity of fluids. This method uses all of the physical and theoretical elements of the previous method. The "made easy" method do not needs a continuous sweeping of the distance L, between the generator and the sensor to perform the measuring. Not only this characteristic, on the "made easy" method, the continuous recording of the sensor signal $V_N$ as a function of the time, results in a continuous recording of a thermal property as a function of the time. Therefore, the thermal diffusivity for the statement method is given by the expression:

$$\alpha = \frac{\alpha_{air}}{\left[1 - \frac{\ln V_n}{L(\pi f/\alpha_{air})}\right]},$$

in which $\alpha_{air}$ is the thermal diffusivity of the air, $V_N$ is the normalized signal obtained during the measuring, L is a fixed distance keeps between the sensor and the thermal waves generator, f is the modulation frequency the of thermal waves generator. This method is shown in more details in: Monitoring Of Gas Diffusion In Air Using TWI Technique: Thermal Diffusivity Measurements Made Easy J. A. P. Lima, M. G. Da Silva, M. S. O. Massunaga, S. L. Cardoso, E. Marin, H. Vargas And L. C. M. Miranda *Rev. Sci. Inst,* 74, 1 (2003).

According to the present invention, It also exists the possibility of to be performed in the system for thermal properties measurement of fluids, another measurement mode with the such system, in other words, it is the possibility of substituting the thermal waves generator disk for a very thin laminule that be transparent to the exciting radiation range of the source or laser. Unlike what it happens in the aluminum disk configuration, the laser beam crosses the transparent laminule reaching directly the whole area of the sensor. In this case, the thermal wave is generated on the sensor surface and not on a thermal waves generator disk surface. In those conditions, the thermal property that influences the sensor signal is the thermal effusivity and not the thermal diffusivity.

According to the present invention, an another configuration using the same elements of the previous method, it can perform a selective monitoring of specific substances by means of the appropriate selection of the wavelength of the light source or laser. Not only the appropriate selection of the wavelength it is also necessary to select an appropriate frequency of modulation so that the signal of the sensor, be only sensitive to the optical absorption coefficient of the measured substance (liquid or gas). This way, the concentration of the substance under interest can be monitored.

Established the theoretical principles, for the purposes of illustrating the invention, there are shown in the drawings forms which are presently preferred, it being understood, however, that the invention is not limited to the precise arrangements and instrumentalities shown.

Figure 1:
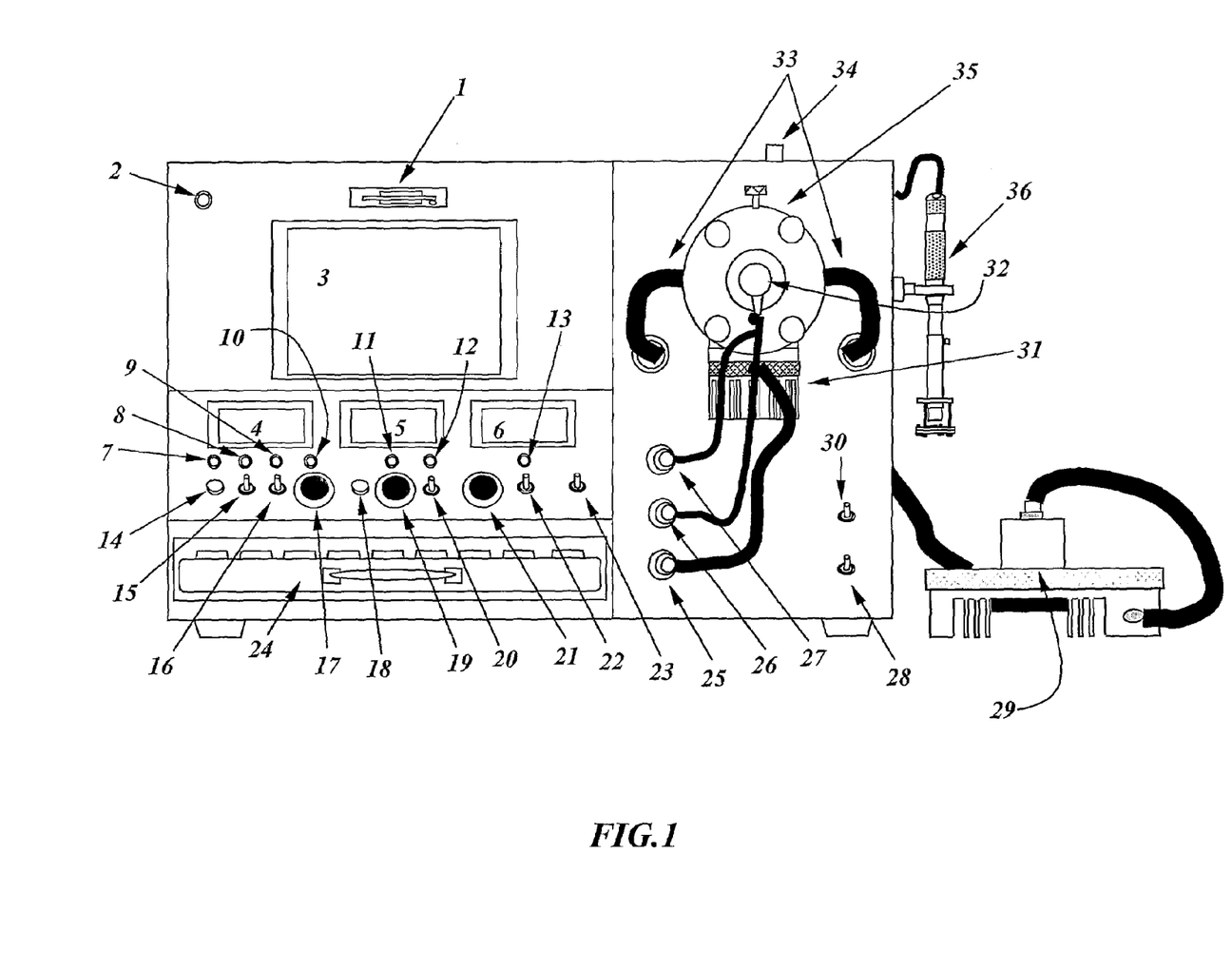
FIG. 1 shows the front view of the system, on what it can be seen out the display, the control panel, the analysis chamber as well as the movable probe and the prethermalizador device.

With reference to FIG. 1, the disk drive is shown (1); indicative pilot lamp of energized system (2); screen (3); prethermalizador/sample holder temperature display (4); laser diode current/voltage display (5); analysis chamber temperature display (6); flashing LED to inform the prethermalization temperature is reached (7); LED (bicolor) to inform the temperature controller activity of the sample prethermalizator device (8); LED (bicolor) to inform the temperature controller activity of the sample holder (9); sample holder standby indicative LED (10); LED to inform the laser diode power supply is enabled (11); flashing LED to inform the laser diode modulation is turned on (12); LED (bicolor) to inform the temperature controller activity of the system of thermal stabilization of the chamber (13); momentary button to make available the sample prethermalizator device temperature on the prethermalization/sample holder temperature display (4) (14); on/off switch of the sample prethermalizator device's Peltier (15); on/off switch of the sample holder's Peltier (16); potentiometer for adjusting the sample holder temperature (17); momentary button to make available the laser diode voltage on the current/voltage display (5) (18); potentiometer for adjusting the polarization current of the laser diode (19); on/off switch of the laser diode modulation of (20); potentiometer for adjusting the analysis chamber temperature (21); on/off switch of the analysis chamber's Peltier (22); switch to enable the movable probe or the analysis chamber (23); retractable keyboard (24); socket for the sample holder plug (25); socket for the thermal wave cannon plug (26); socket for the sample holder movable recipient thermocouple plug (27); on/off switch of the system of thermal stabilization of the chamber's pump (28); sample pretermalizador device (29); on/off switch of the analysis chamber's exhaustor (30); sample holder (31); thermal waves cannon (32); hoses for circulation of thermal stabilization fluid (33); handle of the sliding door for access to the internal micrometer or to the distance reference stems (34); analysis chamber (35); movable probe (36).

The following detailed description is of the best presently contempled mode of carrying out the present invention, This description is not intended in a limiting sense, but is made solely for the purpose of illustrating the general principles of the invention.

Figure 2:
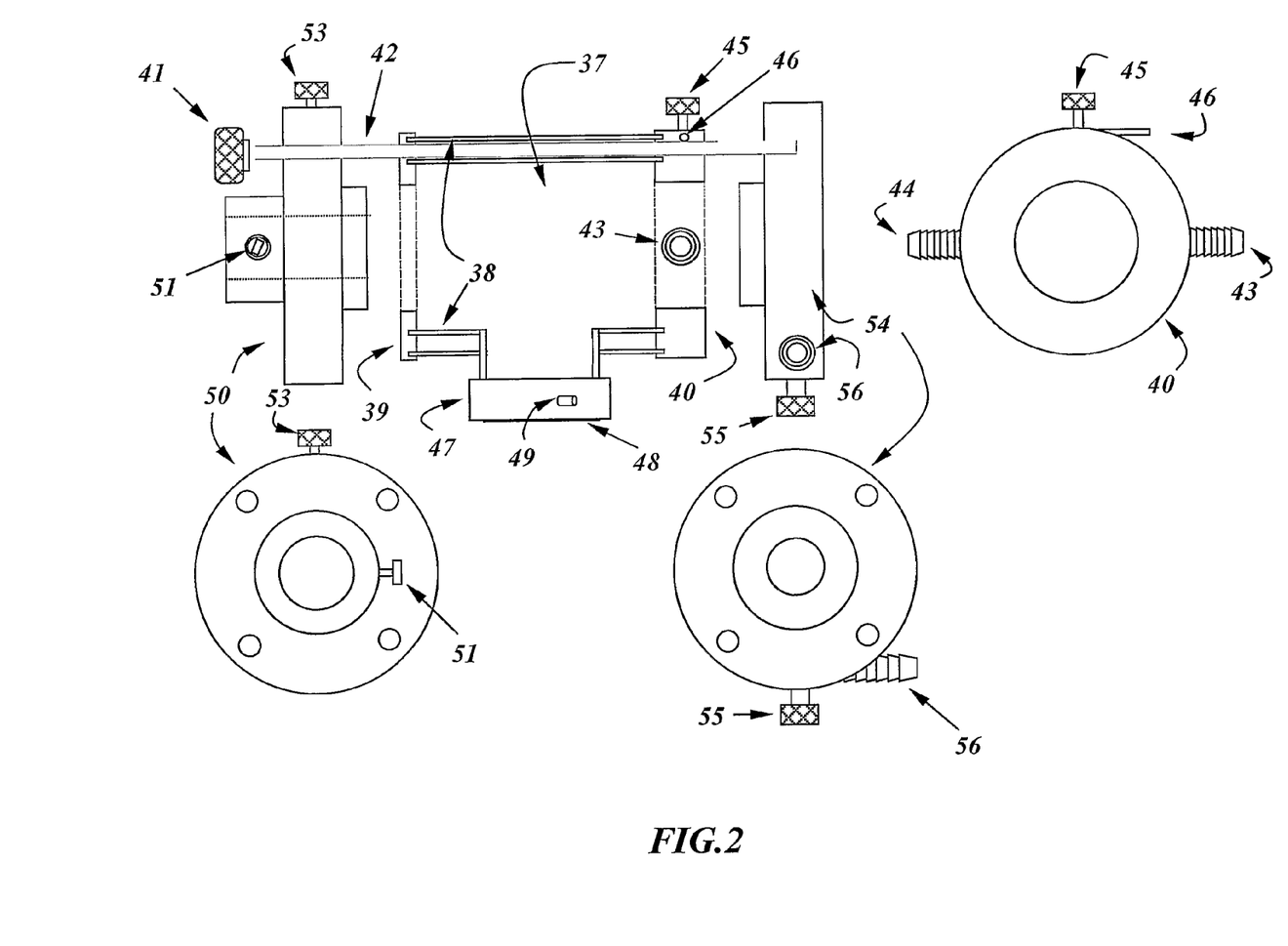
FIG. 2 shows the analysis chamber (A.C) and their respective parts.

According to a not limited mode of carrying out the invention, the analysis chamber 1, FIG. 2, is composed by a flask 37, made preferentially of transparent glass, in "T" shape, with double wall 38 for the circulation of a fluid for thermalizing. At the two extremities of larger diameter of the flask, two rings are glued 39 and 40, which are endowed with grooves to the fit in the borders of the glass part. Interconnecting the two rings, there are 4 steel stems (they are not visible in the drawing), whose purpose is to assure the parallelism among these rings and to prevent that the glass part be broken by compression excess during the it fixation. The flask is maintained fastens in it position by means of 4 nuts 41 and 4 fixation screws 42 (only one of the nuts and one of the screws is visible in the drawing). On the periphery of the ring 40 are 2 adapters 43 and 44, in which they are connected to the hoses that drive the thermalization fluid. In this same ring, there is a valve screw (45) and a drain (46) for the passage of air and excess of thermalization fluid during a load or discharge procedure. Glued on the inferior opening of the flask, there is a ring (47) endowed with a "O" ring (48) and clamp pins (49) to fitting in the sample holder. The flask can be made of several materials, but preferably was used the aluminum to making the rings, and the glass, for its low residues adherence. This assembly, not only allowing the continuous visualization of the state of the cannon and of the sensor, but it facilitates the cleaning for the user.

According to the invention, the chamber is also composed by a subsequent flange (50), preferentially made of aluminum, having one channel, through which the thermal waves cannon is introduced and locked by means of one screw (51). The flange possesses 4 holes for the passage of the fixation screws (42) (only one of them is visible in the drawing), and a screw valve (53) (V1) for relief of the pressure inside the chamber during the placement or removing of the sample. This valve may be automated by means of solenoid for the user's larger convenience.

The such chamber, possesses still a second flange (54), having 4 holes for the fixation screws, whose function is the global support of the whole array. This flange possesses a central channel through which passes and it slides the cylindrical body of the thermal waves sensor. On the second flange there is a screw valve (55) (V2) with the purpose of obstructing the passage between the internal chamber atmosphere and the pipe that it is connected to the vacuum pump for cleaning the chamber. The connection is made by means of an adapter (56) whose channel is extended to the interior of the chamber. This valve may be also automated by means of solenoid for the user's larger convenience.

According to the invention, the analysis chamber is a totally dismountable device whose purpose is to provide an isolated atmosphere and constant volume. The effective volume of the chamber may be between 50 to 1000 ml, preferentially a volume of 80 ml was used. The analysis chamber is the place inside of which is performed the analysis of samples such as: mixture of air with volatile liquids vapor, gases, steams or exhaled gases from solids and liquids. With some adaptations and modifications, the chamber may be flooded with the liquid to be measured. In some cases, it can have interest in measuring substances under higher pressures than one atmosphere, or under an initial vacuum condition or of rarefied atmosphere. That is possible, as long as the structure of the chamber and their associated parts are reinforced.

Figure 3:
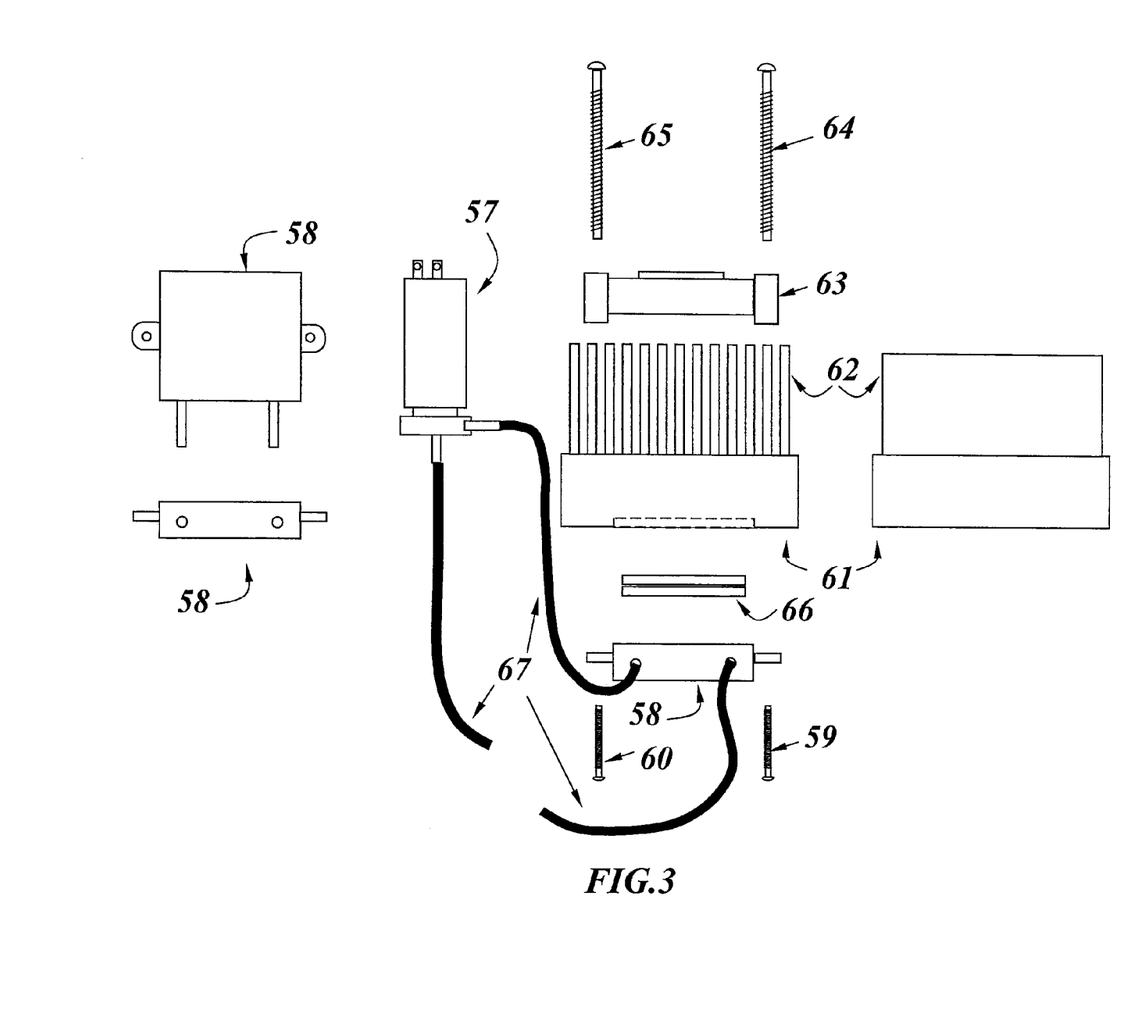
FIG. 3 shows the parts that compose the system of thermal stabilization of the chamber (S.T.S.C).

According to a not limited mode of carrying out the invention, the system of thermal stabilization of the chamber, that it can be seen in FIG. 3, consists of a pump 57, being preferentially of centrifugal type, of small size, and to using in DC; a reservoir 58, fastened by means of screws (59) and (60), preferentially made of copper, squared shape, with pipes for entrance and exit of liquid; a radiator (61) being preferably rectangular and of aluminum, having fins (62); a fan (63) being preferentially of 12V DC, fastened by means of 4 screws (only the screws (64) and (65) they are visible); one Peltier element (66) being preferentially square, and hoses (67) for the circulation of the fluid.

According to the invention, the system of thermal stabilization of the chamber is based on a closed circuit of forced circulation of fluid by means of pump and transported by means of hoses. The efficiency of the radiator is improved by the forced passage of air through the fins of the radiator. The used fluid may be a mixture of etilen glicol with water or water pure only. The purpose of such system is to maintain constant the temperature inside the chamber's wall and also to create the favorable conditions of humidity necessary for determined types of measure.

Figure 4:
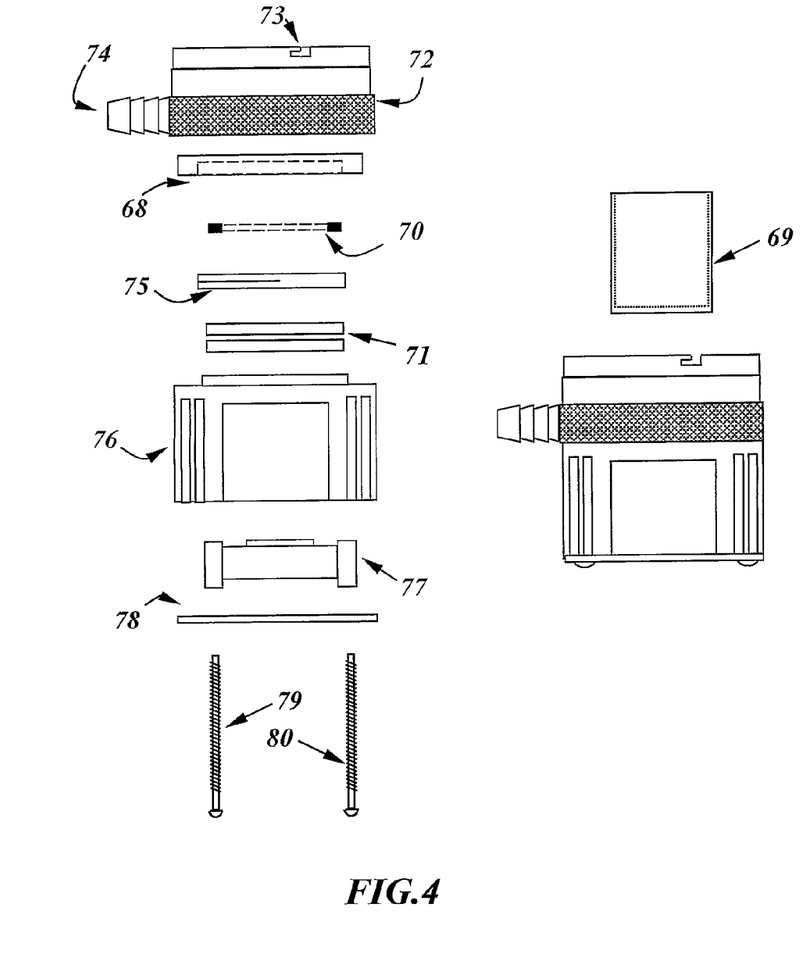
FIG. 4 shows the sample holder (S.H).

According to a not limited mode of carrying out the invention, the sample holder, shown in FIG. 4, consists of a support (68) with cylindrical shape similar to a flange. This part, preferentially made of teflon, works as a guide that allows the alignment of the movable container of the sample holder (69) with the opening of the chamber. The support (68) possesses a circular groove for a "O" ring (70) and a low squared relief with windowsill. This low relief is for the insertion of a Peltier element (71), that it is the responsible active element for the thermal stabilization of the sample.

Another part of the sample holder is a ring (72) which is made preferentially of aluminum and that it is fit to the part (68), involving it. This part possesses two rifts (73) diametrically opposed, being adjusted to the two pins in the periphery of the opening of the analysis chamber, allowing to the user the fast setting of the sample holder on the measure position. The such part possesses a lateral pipe of exit (74) for the passage of the Peltier element's wires, the thermocouple's wires, the fan's wires and the wire of the detection circuit of the sample holder in the measure position.

The sample holder also possesses a circular tablet (75), preferentially made of copper, and having a channel of 2 mm of diameter that extends to the center. The tablet works as a middle of thermal contact between the bottom of the movable container and the element Peltier, not only housing a thermocouple inside of the channel of 2 mm, whose signal is sent to the circuit of the temperature controller.

In the such sample holder, there is a cylindrical radiator (76), endowed of fins, on the upper region exists a circular high-relief over which the surface of the Peltier element is attached by means of a thermal paste. Inside the part, and among the fins, exists a low relief with squared shape, whose purpose is to accommodate a mini-fan (77) that it forces the circulation of air through the fins of the radiator. In the bottom of such part there is a protection screen (78) for the fan. All parts are kept fasten by means of 4 screws (only the screws (79) and (80) are visible in the drawing).

According to the invention, the sample holder is the device that it works as support of the movable container that containing the sample. The movable container has capacity to receive 10 ml of liquid sample and it may also receive solid samples. The sample holder also allows the seal of the internal atmosphere of the analysis chamber and the ambient air. Not only of those functions, the sample holder provides the thermal conditioning of the sample during a measure, and keeping it in a constant temperature. This constant temperature can have two values. All time in which the sample is in the standby position, in others words, disconnected of the chamber, the movable container of the sample holder is maintained in a fixed temperature that can be the same one of the prethermalizador device and that it is adjusted by the user by means of a precision trimpot embedded in the back panel. When the sample holder is connected on the chamber, automatically the controller receives a command and it adjusts the temperature of the sample holder for a new value that is softwaremed by the user by means of a potentiometer ((17) FIG. 1). The sample holder is also provided of cable with connector, allowing this way the connection to the lateral front panel of the system ((25) FIG. 1). Therefore, it carries him/it sample as a whole is a replacement component, could be substituted in the complete by another one.

Figure 5:
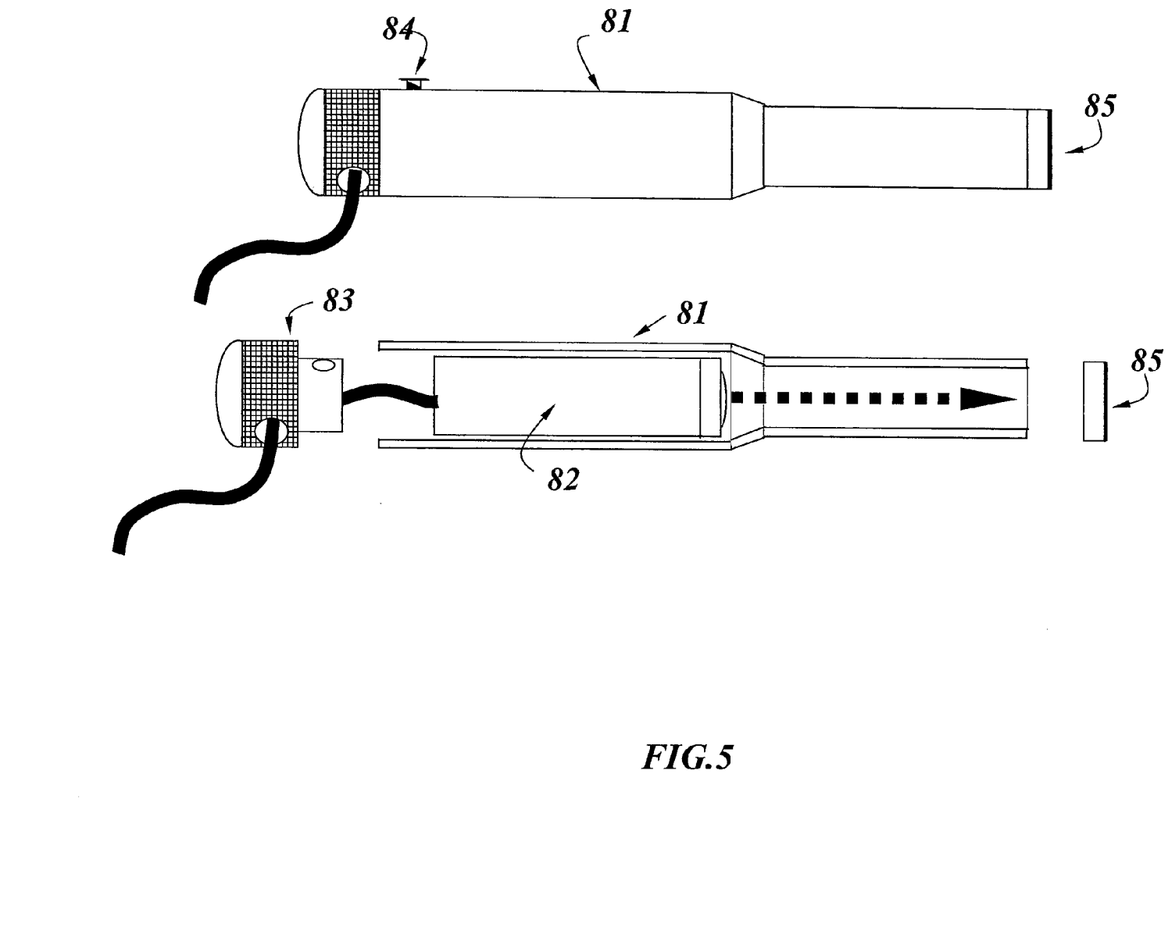
FIG. 5 shows the thermal waves cannon (T.W.C).

According to a not limited mode of carrying out the invention, the thermal waves cannon, FIG. 5, consists of a tubular body (81) in whose interior lodges a small laser diode cannon (82) endowed with lens for focalization. The cannon laser diode is introduced through the back opening that receives a protection cover (83) that is locked by means of a screw (84). The front opening of the cannon is covered with the thermal waves disk (85). The such disk may be made preferentially of a 0.015 mm thickness commercial aluminum foil stretched and glued on the border of a aluminum ring. The face of the disk gone back to the internal part of the pipe must receive a thin layer of black covering with high optical absorption. Preferentially the covering should be the black of the soot since this material possesses the highest optical absorption coefficient.

According to the invention, the thermal waves cannon has as function to generate the thermal waves necessary for performing the measures. The generated thermal waves depend on the form of wave of the current (sinusoidal, square, step or impulse) that is sent for the laser diode, or excitement source, or of heating, and depends on of the frequency and of the focus. The thermal waves cannon can generate frequencies from 0.1 to 1000 Hz, but for most of the cases involving measures of vapors and gases, the preferential frequency to be used is of 10 Hz. Not only this, it is necessary that the focus be adjusted in order to illuminate all black area of the disk of aluminum. The purpose of this fitting is to induce the generation of plane thermal waves front. The assembly type suggested here for the generator disk provides the easy removal and the substitution of the same in case of flabbiness, perforation or accumulation of residues. The thermal waves cannon is also provided a connector cable allowing its connection to the lateral front panel of the system (26 FIG. 1). Therefore, the thermal waves cannon as a whole is a replacement component, and may be substituted entirely by an another one.

Figure 6:
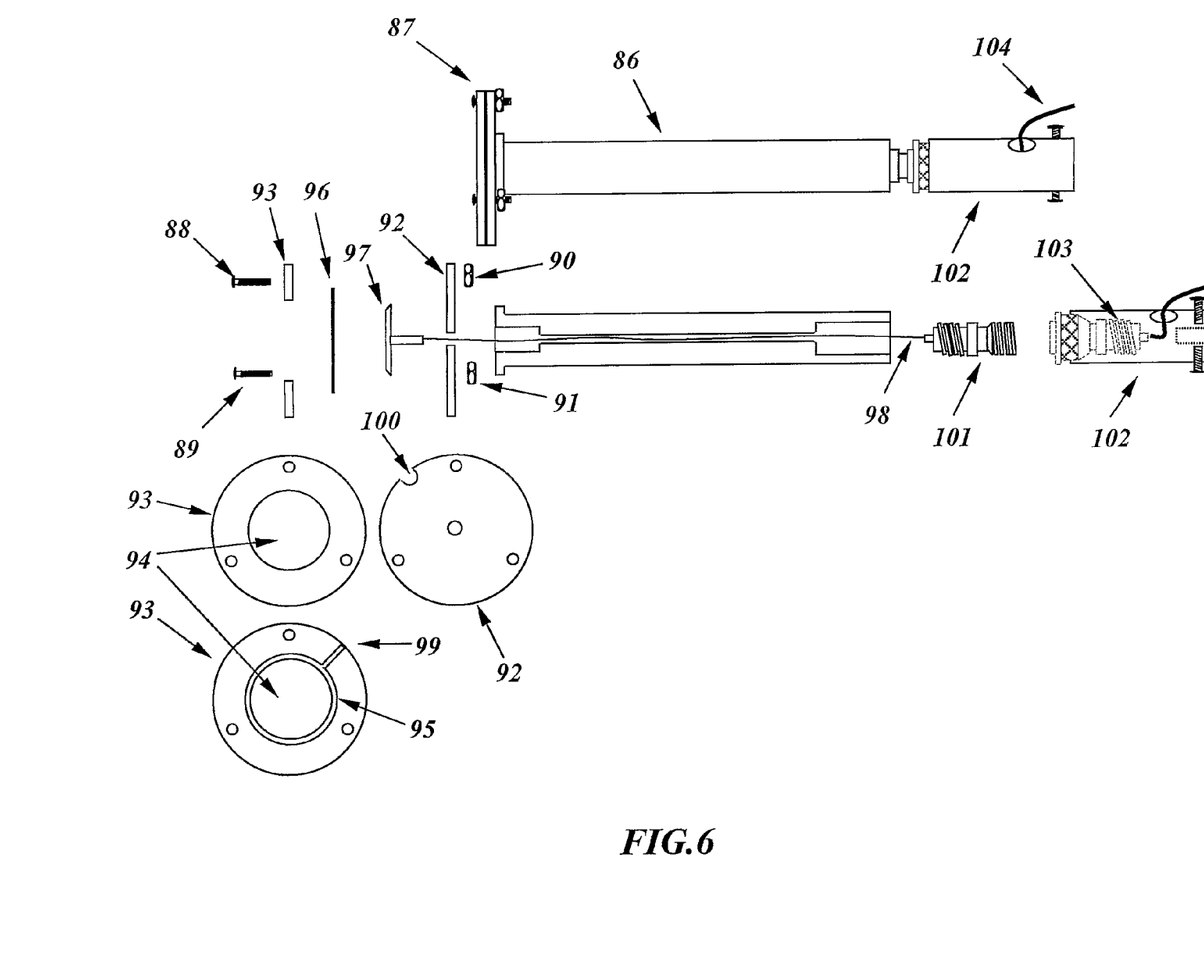
FIG. 6 shows the thermal waves sensor (T.W.S).

According to a not limited mode of carrying out the invention, the thermal waves sensor in FIG. 6 is constituted of a body, preferentially made of brass (86), whose extremity is adapted to a circular head (87) that is constituted of several other components. The circular head possesses two disks made preferentially of fiber printed circuit board and that are fixed each other by means of 3 screws and 3 nuts (only the screws (88), (89) and the nuts (90), (91) are seen in the drawing). The first disk (92) is fastened to the brass body. The second disk (93) (frontal) possesses the same diameter and thickness of the first one, however, it differs of the other one for the fact of possessing a wide central hole (94) and a conductive track of copper (95) for electric contact with one of the metallic faces of the disk of PVDF (pyroeletric sensor) (96). In contact with the other metallic face of the disk of PVDF, exists a brass pin (97) soldered to the output connector by means of a wire (98). The electric loop of the circuit is made by means of a thin ground wire soldered in the derivation (99) of the trail (95) of the front disk (93), passing through the chamfers (100), and that is a soldered to the body of the sensor (86). After the circular head (87), the borders of the disks, the areas around of the screws heads, nuts, periphery of PVDF and soldering points of the ground wire, be assembled, they should receive a impermeable protective resin. Glued on the final extremity of the sensor there is a connector (101) with a thread type connection. Another part exists (102), with a embedded female type connector (103) which is soldered to a cable (104) and connected to the measure circuit. This part allows the adaptation of the sensor to a micrometer head. The micrometer head type have to be of a non rotative spindle type in order to avoid the rotation of the cable during the distance fitting.

According to the invention, the sensor is the component whose function is to pick up the thermal waves, which is generated by the cannon and to convert them in a correspondent electric signal. The electric signal when measured, translates it in a greatness that is sensitive to the variation of the thermal property of the measured substance. The main component of the sensor is a material pyroeletric. For use in the present invention, the preferential material is the β-polivinyliden difluoret (PVDF). The main characteristic of the b-PVDF is its easy cut in any format, not only it, but it presents a weak piezoelectric component in relation to the pyroeletric one. Some ceramic materials are also pyroeletric as the barium titanate and the zirconate lead titanate and alternatively, they may be used. The possibility of using a microphone as detector can also be another alternative. Depending on the frequency with that the sensor is exposed to gaseous or liquid aggressive substances or even for continuous exhausting use, the sensor will need to be replaced. The connector type suggested in the present invention allows to the users of the system to substitute the sensor easily for an another new one. Therefore, the sensor as a whole is a sealed replacement component, and must be completely replaced for other one in case of damage, bad operation or wear and tear.

For the necessary positioning of the sensor in relation to the thermal waves cannon, in fact, there is no need that the micrometer have to be digital, however, some of those models possess digital data output. In this case, it is possible to send them for the CPU of the system. In fact, for the present invention it can spare the inclusion of a micrometer, as long as there is some type of reference cursor by means of which the distance between the sensor and the thermal waves cannon can be adjusted accurately and maintained stable.

Figure 7:
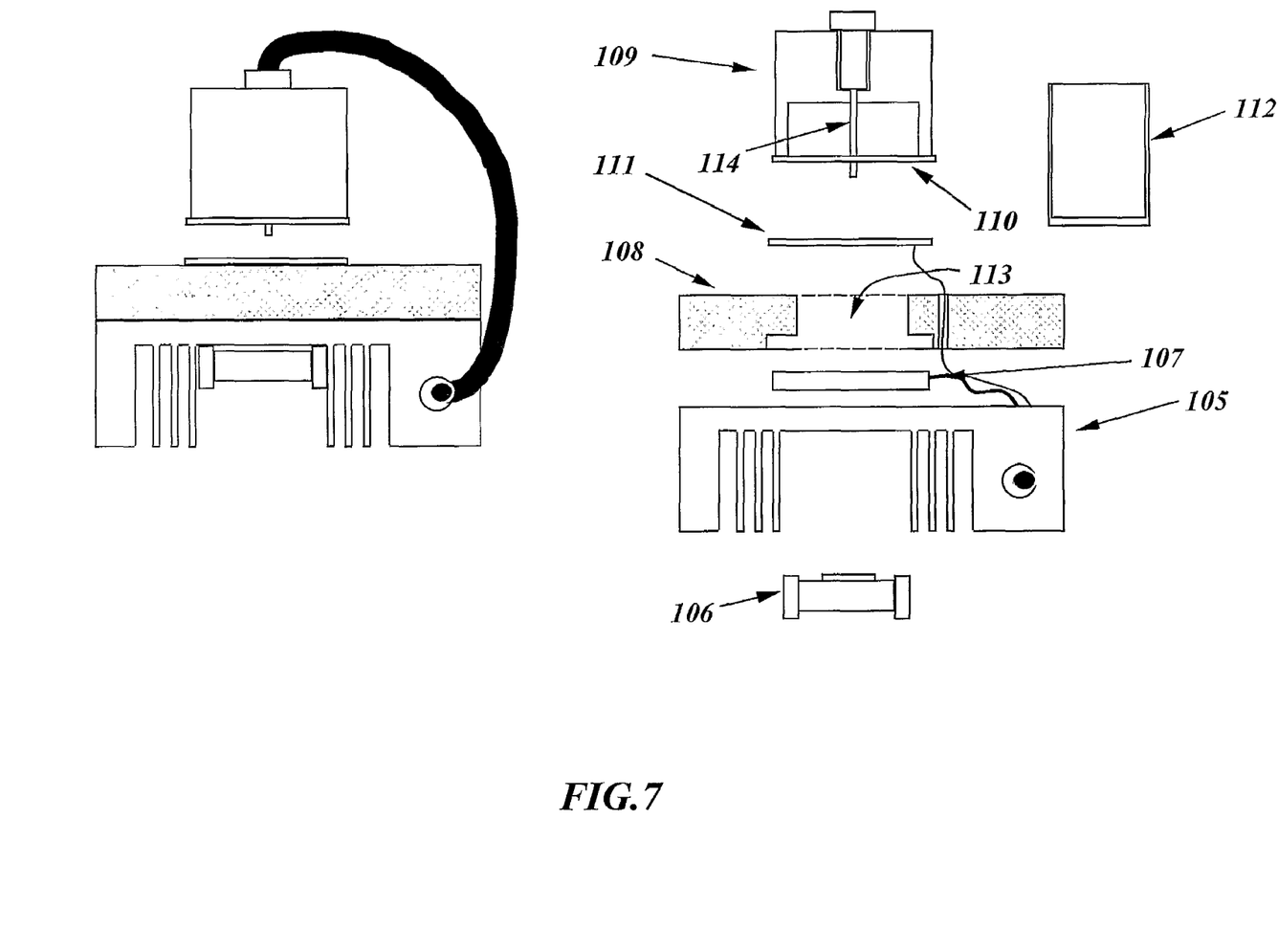
FIG. 7 shows the sample prethermalizador device (S.P.D).

According to a not limited mode of carrying out the invention the device prethermalizador FIG. 7, consists of a metallic base (105) endowed with fins. Among the fins, a space exists where a mini fan is embedded (106). On the such base, a Peltier element (107) is attached and is fastened by means of thermal paste. Involving the element Peltier, a foam block exists for thermal isolation (108) that adapts to the outline of the statement element. The foam block is fastened to the base (105) by means of glue. Around of the circular opening of the foam and of the cover (109), two metallic rings exist (110) and (111) soldered each one in a thread. The device is endowed with movable container (112) with capacity to receive 20 ml of liquid sample. The container is inserted in its receptacle (113). Inside the cover a thermocouple exists (114) which is in direct contact with the liquid sample.

According to the invention, the prethermalizador device makes the thermal conditioning of a sample before it to be put in the sample holder and to be taken to the chamber for the accomplishment of a measure. The prethermalization process only has beginning when the cover is put on the movable container. The cover (109) that is put on him referred movable container avoids the exhibition of the sample to the atmosphere during the prethermalization process. The rings (110) and (111) work as an electric key for automatic activating of the prethermalization process. The thermal conditioning is necessary to guarantee that all of the samples, for a certain measure type, be in the same initial condition of temperature before they be taken for the chamber. The reference temperature that must be maintained constant by means of the temperature controller is the temperature of the surface of the liquid contained in the movable container. The prethermalizador device also possesses a cable with connector in its extremity to connecting to the back panel of the instrument. The prethermalizador device as a whole, is a replacement component and so may be substituted completely by an another one.

Figure 8:
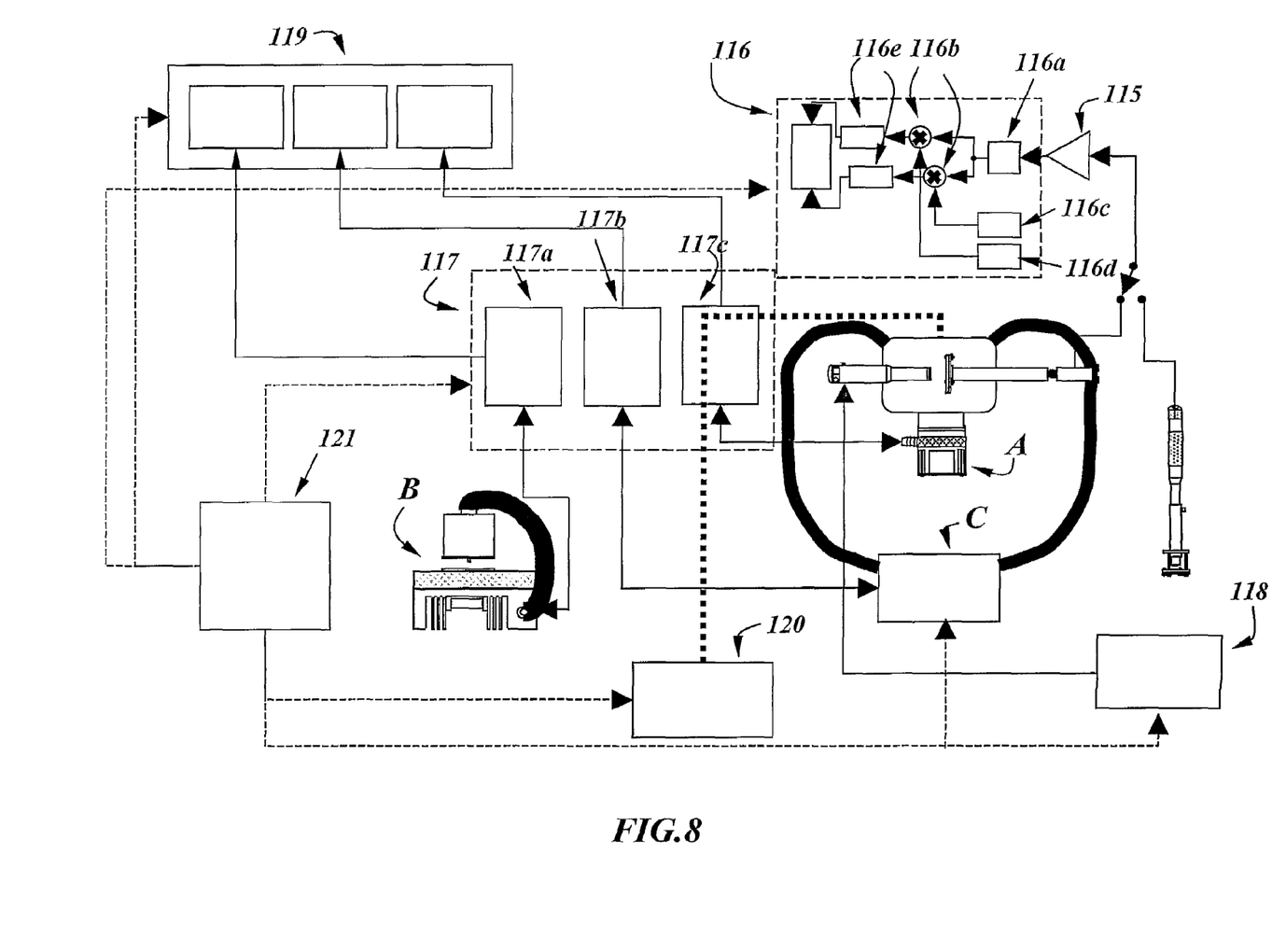
FIG. 8 shows the system of measure and control (S.M.C).

According to a not limited mode of carrying out the invention, the measure system and control, FIG. 8, becomes separated in 7 blocks.

The first block (115) consists of a transimpedance preamplifier that can be based on the integrated circuit TI 081. The function of this circuit is to amplify the low signal of originating from current the sensor or of the movable probe and to turn it compatible with the stage of synchronous detection.

The second block (116) consists of a synchronous detector. The basic components of this healthy detector: filter band pass (116a), multipliers (116b), sinusoidal generator (116c), generator cossenoidal (116d) and raisin-low filters (116e). The circuit for this detector can be based on the integrated circuit AD 534 that is an analogical multiplier of precision. The sinusoidal generators and cossenoidal can be implemented with a digital accountant, converter D/A and memoirs EPROM. The filters can be based on the integrated circuit TL 084. The module extractor and angle can also be implemented also with AD 534, EPROM and converter D/A. The synchronous detecting block is also susceptible to be implemented by means of a software that receives the measured values by means of a circuit or plate A/D. It still exists the possibility of the use, for example, of a detecting commercial plate synchronous of the type OL 4000 for PC. In these last two options, the synchronous detector stops belonging to the measure system and control and raisin to do part of the microprocessamento system.

The third block (117) consists of the temperature controller. This block is composed by 3 controlling circuits of temperature (117a), (117b) and (117c) based on the integrated circuit AD 590 that converts the voltage of a thermocouple directly in a voltage proportional to the temperature of the process to be controlled. That voltage is compared then with the softwareming temperature by means of a voltage comparator using an integrated circuit TI 081. Of this it sorts things out, the voltage resulting from the comparison is sent for a power driver that feeds directly the Peltier element. The 3 circuits are independent, being each one for each function, in other words, to control the temperature of the sample holder A, of the device prethermalizador B and of the system of thermal stabilization of the chamber C.

The fourth block (118) it consists of a source/modulator whose function is the feeding and modulation of the diode laser. The source for feeding of the diode laser is of the constant average type whose circuit is based on the integrated circuit TL 081 and in the transistor TIP 122. The circuit of the source should possess devices of safety such an as:

The increase of the current should be made by means of a multi-turns potentiometer (or equivalent electronic circuit that it allows soft variation) in order to avoid her burns accidental of the diode laser for abrupt ascent of the current.

To impede the activating of the laser after a lack of energy of the net electric case the potentiometer (or electronic circuit) it has been left in a value of larger current than 1% of the maximum current.

As modulator of the diode laser, in this case, a transistor TIP 122 was used to drain cyclically the current of the diode laser for the earth. The form of chosen wave for the modulation of the diode laser was the square wave. The wave, injected in the base of the transistor, it is generated by a softwaremable oscillator to crystal of quartz based on the frequency divisor integrated circuit NE 4059.

The fifth block (119) it consists of 3 display panels cases with 3½ digits. Such display cases can be liquid crystal or of LED. In both cases, they can be implemented with the circuits integrated CI 1705 or CI 1706, or they be acquired in commercial modules already ready for installation and use.

The sixth block (120) it consists of a vacuum pump, preferentially of diaphragm and of continuous current 24V, whose purpose is to renew the air of the chamber contaminated by the last measured sample. The pump is connected to a circuit electronic timer that turns off it automatically in 5 minutes after it being worked by the user.

The seventh block (121) it consists of a exclusive power supply, preferentially of the switched type, with multiple exits and with independent fuses for each block of the referred measure system and control.

According to the invention, the measure system and control is entrusted by all of the functions not computing involved in the measure of thermal properties. The whole system is energized by means of an independent general on/off switch, located in the back panel.

Figure 9:
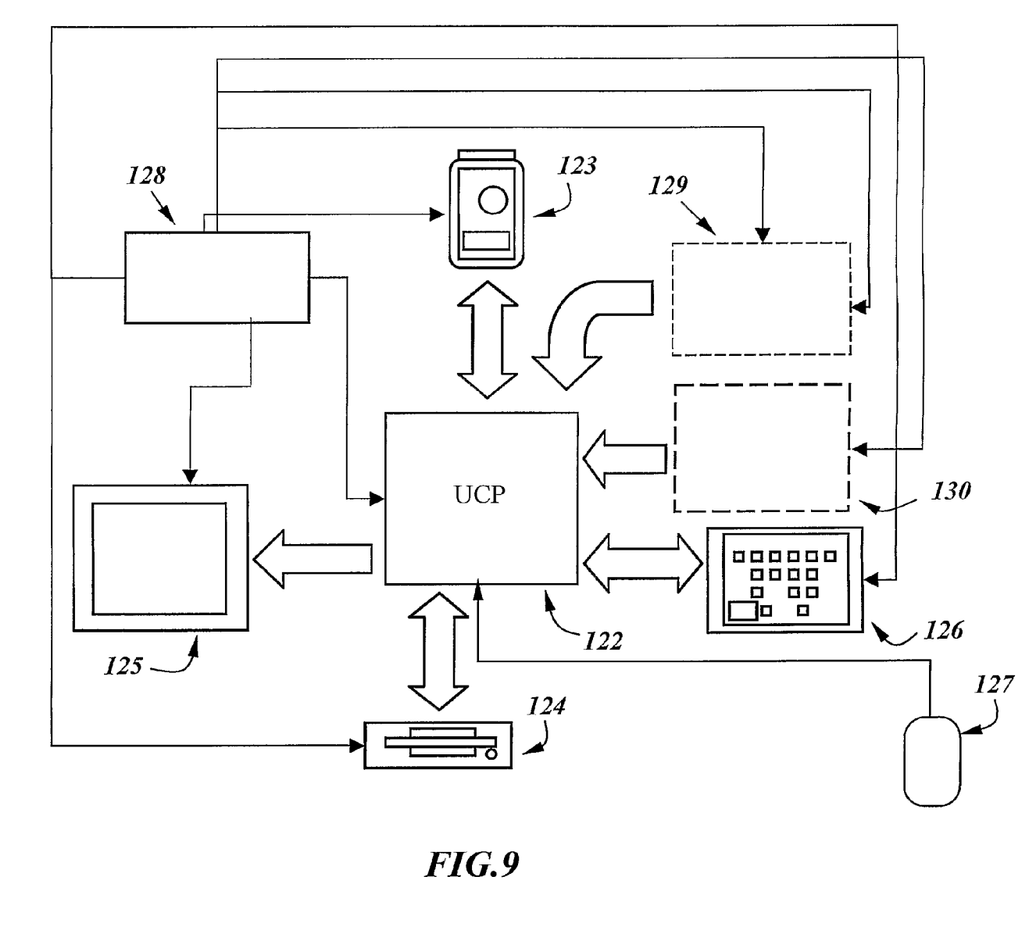
FIG. 9 shows the microprocessing system (M.S).

According to a not limited mode of carrying out the invention the microprocessing system, FIG. 9, becomes separated in 7 blocks.

The first block (122) consists of a central processing unit that can be commercial board with bus type ISA/PCI, or microprocessed system dedicated to accomplish the necessary functions to the operation of the system for measurement of thermal properties of fluids. In both cases, it owes if to have as minimum requirements: a processor of 133 MHz, 16 Mb of RAM memory and hard disk with 100 Mb of memory. Preferentially the block (122) it can be a commercial standard system MOP 104 that not only being more compact, it can work with a hard disk (123) in solid state avoiding the loss of the data this way in case the system suffers some fall type or impact.

The second block (124) consists of an unit for recording and reading of data for the external transfer or acquisition of the measures files or data of the equipment. In this case the options can be a flexible disk drive 3½", Zip or of CD.

The third block (125) consists of a screen or monitor that it makes possible the clear visualization of the graphics exhibited by the softwares installed in the system. Preferentially the display can be of the type TFT 6×5" colored that is compact, it presents excellent resolution and shine.

The fourth block (126) consists of a softwaremable mini-keyboard, that should have at least 44 keys and it can be of the type membrane or of buttons.

The fifth block (127) consists of a mouse, being indicate the type trackball preferentially. In this case, the mouse can be built-in in the own keyboard. The other option is the use of a common mouse, linked to the serial door of the plate CPU.

The sixth block (128) consists of a power supply of the type used in PC. This source being exclusive for this system, it impedes that any influence type, interference or noise of the measure system happens.

The seventh block (129) consists of a plate or circuit with multiple entrances and analogical exits. This block is necessary only in the modalities of accomplishment of the system for measurement of thermal properties of fluids in that the functions carried out by the measure system and control be executed by means of a software.

The eighth block (130) consists of a synchronized detection board. This block is necessary only in the modalities of accomplishment of the system for measurement of thermal properties of fluids in that the function of synchronous detection, carried out by the measure system and control, it be executed by means of a software.

According to the invention, the microprocessing system has as function the acquisition of the experimental data, processing, calculations, softwaremings, introduction of data, exhibition of results and graphics, recording and reading of information that you/they are necessary to the operation of the system for measurement of thermal properties of fluids. The system computational has a general on/off switch located independent on the back panel.

Figure 10:
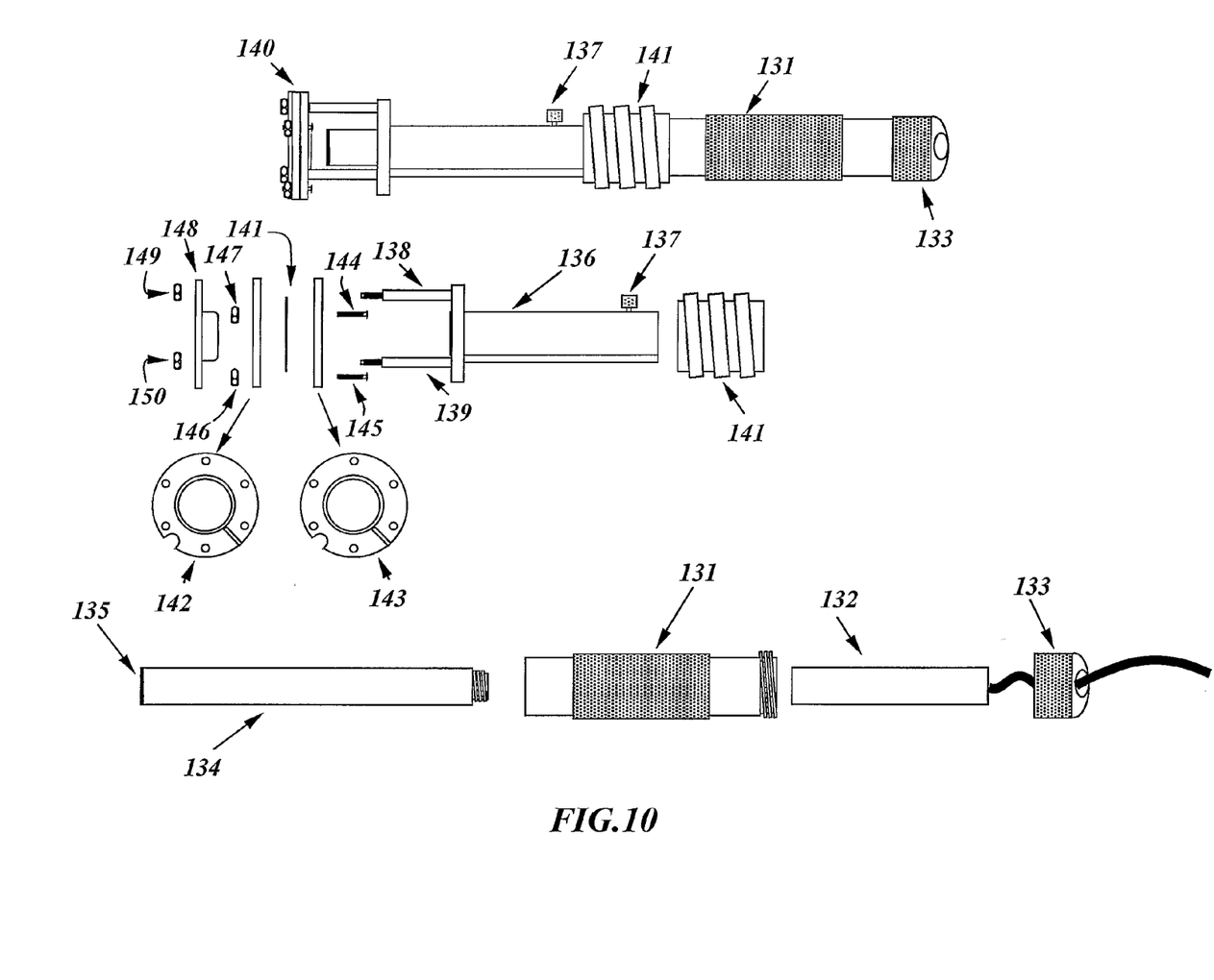
FIG. 10 shows the movable probe (M.P).

According to a not limited mode of carrying out the invention, the movable probe, FIG. 10, is constituted basically of a main cylindrical tube (131) in whose interior lodges a cannon of diode laser or radiation source (132) with lens for focalization. A cover endowed with thread (133) it maintains closed the opening through where the cannon is introduced. Screwed to the main cylindrical tube (131) a longer secondary tube exists (134) whose extremity is covered with the generating disk of thermal waves (135). This part can be made preferentially with a disk of commercial aluminum foil of stretched and agglutinated 0.015 mm of thickness in the border of a ring of aluminum. The face of the disk gone back to the internal part of the tube should receive a black covering with high optical absorption. Preferentially the covering should be the black of the tobacco. The making here suggested for the generating disk provides the easy removal and substitution of the same in case of flabbiness, perforation or accumulation of residues. Involving the longer secondary tube (134), a slippery tube exists (136), with restraint screw (137), possessing in the subsequent extremity a disk with 3 willing stems in triangle (only the stems (138) and (139) they are visible). The said stems sustain the disk (140) where the sensor film of thermal waves is set up and they serve as a middle of passage of the threads of contact of the sensor of thermal waves. The threads continue through a tube until they enter in the main cylindrical tube (131). In order to avoid the exhibition of the threads, a flexible folding hose of protection exists (141) that is fit in among the slippery tube (136) and the main cylindrical tube (131). Coupled to the slippery tube there is a disk of sensor element (PVDF) (141) that is housed among two disks (142) and (143) that are maintained united through 3 screws and 3 nuts which possess copper trails that work as contact electrodes (only the screws (144) and (145) and the nuts (146) and (147) they are visible). After the assembly of the sensor element, a scouring pad is introduced (148), preferably done in teflon, with the purpose of stretching the sensor element so that this is with a high relief frontal. The scouring pad is fixed to the stems through 3 nuts, and just the nuts (149) and (150) they are shown.

According to the invention, the movable probe is one of the devices that composes the system for measurement of thermal properties of fluids. The said probe is especially indicated for measures of thermal properties in liquid means, and depending on fittings, eventually it can be used for measure in gases or vapor. The beginning of operation of the movable probe is exactly the same described for the sensor and the cannon used in the analysis chamber. The modulated light or pressed of a radiation source it happens on the blackened surface of the generating disk of thermal waves (135). The said waves cross the half liquid (or gaseous) and they arrive to the disk of sensor element (PVDF) (141). The amplitude of the signal generated in the sensor is function of the frequency of modulation of the radiation source, of the distance between the sensor and the generating disk of thermal waves and of the thermal diffusivity of the middle in that the probe is inserted. For most of the cases of measures of the thermal diffusivity of liquids, the spacing among the sensor can be of the order of 1 mm and the frequency of modulation 1 Hz.

It is also possible to perform another measurement mode with the movable probe by means of the substitution of the generating disk of thermal waves (135) for a thin sheet that it is transparent for the strip of radiation of the source of used excitement or of a laser. In this case, the thermal wave is generated in the own surface of the sensor (141) and not by means of the generating disk of thermal waves. With this configuration, the thermal property that it influences the signal of the sensor is the thermal effusivity and no the thermal diffusivity.

According to the invention, another configuration using the same elements of the previous configuration, it can turn possible a selective monitoring of substances specify by means of the appropriate selection of the wavelength of the luminous source or of a laser (132). Not only the appropriate choice of the wavelength it is necessary but also the choice of a frequency of appropriate modulation, so that the signal of the sensor is just sensitive to the optical absorption coefficient of the liquid or of the measured gas. This way, the concentration of a substance of interest can be monitored. Due to the fact of the said probe to possess small dimensions and a long connection cable interconnecting it to the main system, the same can be handled easily by the operator and to be taken or installed at some distant place of the system. Likely the other devices of the system, the movable probes as a whole, it is a replacement component and may be substituted completely by another one.

So that the system for measurement of thermal properties of fluids to performs the measurement of thermal properties, is necessary the existence of a resident software containing an exhibition module that makes the acquisition of the measured values for the sensor and make the due processing and calculations, whose results should be presented in an appropriate way for the user. According to a not limited mode of carrying out the invention, the said software can be created to work with the operating system DOS, Windows or Linux, in case the microprocessor system of the present invention uses a processing board, as for example, Pentium, Athlon, etc. The software can be developed in Visual language Basic. In this case, the resident software should exhibit a main screen that you/he/she is carried automatically some seconds after the power switch of the microprocessing system to be called. The main screen should be presented in the form of a graphic screen with horizontal and vertical graduation, exhibition boxes and menu bar.

For the case in that the thermal property to be registered in function of the time is the diffusivity, the horizontal axis of the graphic represents the time and the vertical axis, the thermal diffusivity. The exhibition boxes are in number of 8 and they should show the name of the file of the measure in process, the value of the instantaneous module of the signal of the detector (mV), the instantaneous value of the thermal diffusivity (cm2/s), the value of the real component of the signal X (mV), the value of the component imaginary of the signal Y(mV), the value of the phase (degrees), the modulation frequency (Hz) and the time (s) elapsed of the measure.

The main screen of the software also owes disposal of a menu where the user can access such options as: FILE, START AND CLEAR SCREEN. In the option FILE it is available for the user a field nominated FOLDER, where a series of titles is exhibited. The titles of those folders can be typed in another field denominated NEW FOLDER. Whenever possible, the titles should be chosen in way do her allusion to the nature, origin or to the substances whose files of measures in them are contained. When a folder is selected by the user, the list of the files in her contained it should be visible in a field denominated LIST OF FILES. In the space of another field denominated NEW FILE, a new file can be typed and increased to the LIST OF FILES. In another field, still inside of the option FILE, it should have an option denominated COLORS, in case the screen is colored, and SYMBOLS, in case the screen is monochrome. The existence of such functions has for objective to allow to the user the choice of the color or symbol with that a certain file or files for they will be shown in the screen. Linked to the option FILE should be the commands: SAVE, DELETE, LOAD GRAPHIC AND CLEAR GRAPHIC.

Still in the menu it should have an option denominated CONFIGURATIONS. In this option the user can configure the interval of time between the acquisitions of the points of the measure, the total time of duration of the measure, the inferior limit and the superior of the vertical scale.

Figure 11:
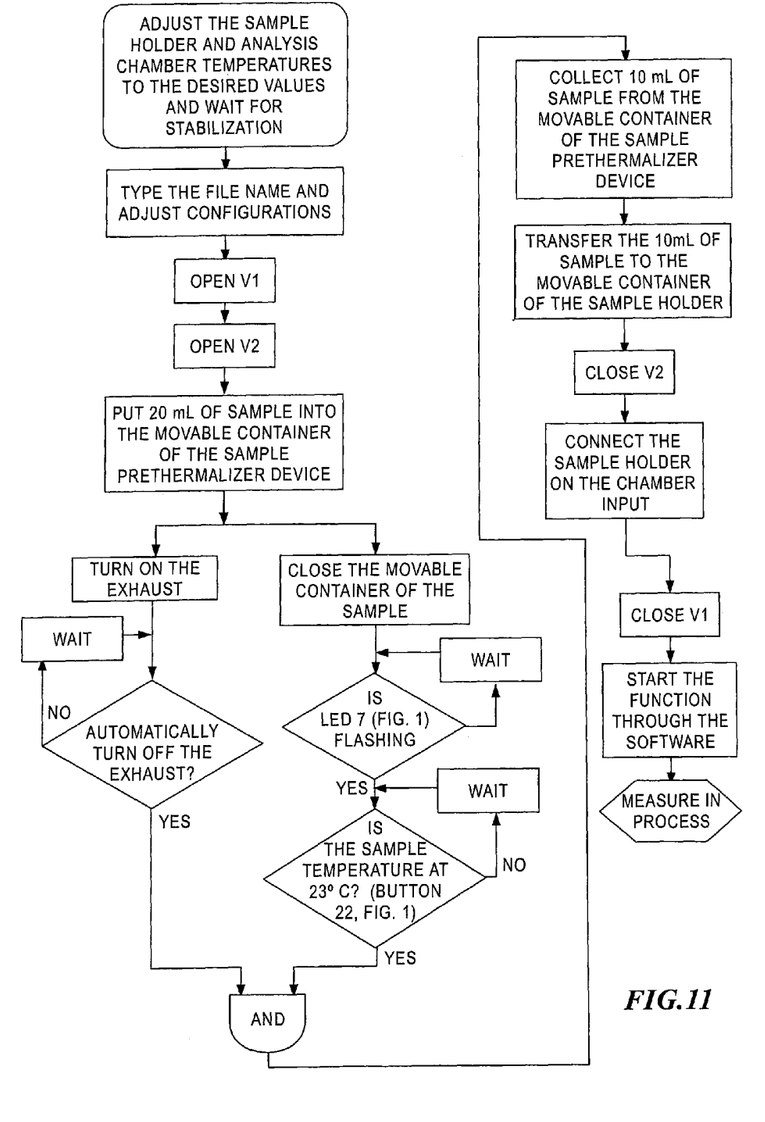
FIG. 11 shows the operation diagram flow.

All of the functions previously mentioned here are considered as minimum requirements so that a measure is accomplished, exhibited in real time and stored. After all of the previous parameters be configured by the user, a measure can be accomplished following the flowchart of FIG. 11.

Another included module in the menu of options is a software for fitting. This software makes calculations and it adjusts with the smallest possible deviation the points generated in a measure to a mathematical model that can be introduced by the user, by means of keyboard, in a denominated field, MODEL. In the field MODEL, it can be inserted and stored an equation that includes a series of way parameters to describe the registered phenomenon. Also in the same field they can be chosen the parameters that they will be exhibited in the vertical and horizontal axis, and this way, to be made a correlation among these parameters. The software FITTING, also includes an option PLOT, that when worked, he/she draws in the screen the result of the model, making possible of this way, a visual comparison between the graphic of the measure and the model made calculations by the software. For the cases of measure of steams of such volatile liquids with gasoline, alcohol, perfumes, etc, or whose model of variation of the thermal diffusivity is adjusted to the simple exponential curve, the methodology denominated conformity" "grating described in the work Photothermal Detection of adulterants in Automotive Fuels J. A. P. Lima, M. S. O. Massunaga, H. Vargas And L. C. M. Miranda Rev. Anal. Chem, 76, 114-119 (2004) it should be used. For the exponential case, the software has the function LEVELS. The function GRATING exhibits a screen and several options where she can select the several files stored that you/they will be used to compose a certain grating. Should the screen also possess a box where the user types the value of the distance (GAP mm) between the generator and the sensor of thermal waves (is the distance adjusted by means of a micrometer). In the making of a certain grating, they will only be able to be used the measures that be accomplished for a same value of "GAP". THE grating a delimited area of a graphic is whose vertical axis represents the constant greatness of decline $\tau$ (seconds) and the horizontal axis, the greatness thermal diffusivity $\alpha$ (cm2/s). This way, for any measure of thermal diffusivity in function of the time that is adjusted to the exponential model, is possible to obtain a value of $\alpha$ (cm2/s) of saturation (value reach in the end of a measure) and constant of decline $\tau$ (seconds). In order to the pair or the several pairs of values can be plotted in the screen, it is necessary first to select a file or files of measures, contained in the LIST OF FILES. After that, the function CALCULATE should be activated. The such function works an interactive algorithm of fitting non linear, for example, of the type Marquardt that adjusts the generic curve of a theoretical model to the experimental points obtained in the measure. In case the exhibition of a report of all of the points $\alpha$ and $\tau$ calculated and plotted for the software, a function HISTORIC should be offered. To clean the screen there is the function to CLEAN SCREEN and to return to the main software, a function, QUIT.

For the making of a grating, the software has a function, to CALIBRATE. For statistics reasons, the software should only allow the calculation of a grating if the number of files of measures selected by the user goes same or larger than 15. Graphically a grating is an squared area or rectangular whose borders are defined for statistical calculation that it take into account the several pairs of values ($\alpha$, $\tau$) measured for an universe of substances of a same type.

To use the function CALIBRATE, it should first to select the files of interest and soon to work the function to CALIBRATE. After at the end of the calculation, it should appear on the screen a column with a series of empty spaces where the user can type a title, that preferably, make reference to the characteristics specify of that grating. Therefore, the information of the grating are memorized and they can be loaded later in the graphic by means of the function GRATING. With this methodology, any new measure of a substance can be tested in relation to a certain associated grating a group of this same substance. This way, it can be verified the parameters $\alpha$ and $\tau$ of the substance in subject do locate inside or out of the said representative grating of the group of substances for which the grating was built.

For the case of measures with the movable probe, all of the previous functions are valid.

The invention claimed is:

1. A system for measuring thermal properties of fluids, the system comprising:
    an analysis chamber, the analysis chamber comprising a flask, a thermal waves cannon support, and a flask support,
        the flask comprising a double-wall, and having a T-shape;
    a system for thermal stabilization of the analysis chamber, said system for thermalization of the analysis chamber being thermally coupled to said analysis chamber;
    a sampler holder configured to receive a sample to be analyzed and to introduce said sample to said analysis chamber;
    a thermal waves cannon configured to generate thermal waves for analysis of a sample disposed within said analysis chamber;
    a thermal waves sensor configured to receive thermal waves generated by said thermal waves cannon and to generate a corresponding signal;
    a sample prethermalizer device;
    a movable probe configured to evaluate a sample; and
    a system of measure and control, said system of measure and control being operatively coupled to said thermal waves cannon, said thermal waves sensor, and said probe, said system of measurement and control comprising:
    a microprocessing system; and
    a resident software for processing and exhibiting data acquired during a measurement.

2. The system of claim 1 wherein the flask is made of transparent glass.

3. The system of claim 1 wherein the thermal waves cannon support comprises:
    a central channel to house the thermal waves cannon;
    a lateral screw for locking of the thermal waves cannon;
    four holes for receiving four fixation stems with endings in thread; and
    a valve screw for relief of pressure in the analysis chamber.

4. The system of claim 1 wherein the flask support comprises:
    a central channel through which the thermal waves sensor slides;
    four holes with thread for receiving the four fixation stems with endings in thread;
    a valve screw; and
    an adapter that connects to a hose of a vacuum pump.

5. The system of claim 1 wherein the flask comprises a previous region, a subsequent region, and an inferior opening, and wherein a previous metallic ring is glued to the previous region, a subsequent metallic ring is glued to the subsequent region, and an inferior metallic ring is glued to the inferior opening.

6. The system of claim 5 wherein the subsequent ring further comprises a central hole for fitting the thermal waves cannon support flange, and two circular channels for fitting the flask.

7. The system of claim 5 wherein the previous metallic ring further comprises:
    a central hole for fitting the flask support flange;
    two circular channels for fitting the flask;
    two holes with adapters for connecting hoses that carry a thermalization fluid;
    a valve screw; and
    a drain for passage of air and expulsion of excess thermalization fluid.

8. The system of claim 5 wherein the inferior metallic ring further comprises:
    two horizontal clamp pins diametrically opposed; and
    a circular channel for a sealing ring.

9. The system of claim 5 wherein at least one metallic ring comprises aluminum.

10. A system for measuring thermal properties of fluids, the system comprising:
    an analysis chamber;
    a system for thermal stabilization of the analysis chamber, said system for thermalization of the analysis chamber being thermally coupled to said analysis chamber;

a sampler holder, the sample holder comprising a metallic support, a second support, a disk, a Peltier element, a base, a fan and a protection screen, said sample holder being configured to receive a sample to be analyzed and to introduce said sample to said analysis chamber;

a thermal waves cannon configured to generate thermal waves for analysis of a sample disposed within said analysis chamber;

a thermal waves sensor configured to receive thermal waves generated by said thermal waves cannon and to generate a corresponding signal;

a sample prethermalizer device;

a movable probe configured to evaluate a sample; and a system of measure and control; said system of measurement and control being operatively coupled to said thermal waves cannon, said thermal waves sensor, and said probe, said system of measurement and control comprising a microprocessing system; and a resident software for processing and exhibiting data acquired during a measurement.

11. The system of claim 10, wherein the metallic support comprises aluminum and is fit in by pressure to the second support.

12. The system of claim 10, wherein the disk is copper.

13. The system of claim 10, wherein the Peltier element heats or cools a sample.

14. The system of claim 10, the base further comprising:
a high relief for support of the Peltier element; and
dissipation fins.

15. The system of claim 10, wherein the fan is embedded in a cavity among dissipation fins, and is connected to a block radiator through screws that pass among the dissipation fins.

16. The system of claim 10, wherein the protection screen is in striped form.

17. The system of claim 10, wherein the second support comprises polytetrafluoroethylene.

18. A system for measuring thermal properties of fluids, the system comprising:
an analysis chamber;
a system for thermal stabilization of the analysis chamber, said system for thermalization of the analysis chamber being thermally coupled to said analysis chamber;
a sample holder configured to receive a sample to be analyzed and to introduce said sample to said analysis chamber;
a thermal waves cannon configured to generate thermal waves for analysis of a sample disposed within said analysis chamber;
a thermal waves sensor configured to receive thermal waves generated by said thermal waves cannon and to generate a corresponding signal;
a sample prethermalizer device;
a movable probe configured to evaluate a sample, wherein the movable probe comprises a main cylindrical tube, a thermal waves source, a cover, a secondary tube, a slippery tube, a disk of sustentation of the sensor, a protection hose and a scouring pad; and
a system of measure and control; said system of measurement and control being operatively coupled to said thermal waves cannon, said thermal waves sensor, and said probe, said system of measurement and control comprising a microprocessor system and a resident software for processing and exhibiting data acquired during a measurement.

19. The system of claim 18, wherein the main cylindrical tube houses the thermal waves source, and further comprises a thread at one extremity for fitting the cover, and a thread at the opposite extremity for fitting the secondary tube.

20. The system of claim 18, wherein the thermal waves source is selected from the group consisting of a diode laser endowed with a focalization system, a source radiation module, a source heating module, direct heat generated by a resistance connected to a variable source, and a thermoelectrical element.

21. The system of claim 18, wherein the cover comprises brass.

22. The system of claim 18, wherein the slippery tube comprises steel.

23. The system of claim 18, wherein the scouring pad comprises polytetrafluoroethylene, and further comprises three holes for receiving three threaded extremities of three stems protruding from the slippery tube.

* * * * *